United States Patent [19]

Dapperheld et al.

[11] Patent Number: 5,100,520

[45] Date of Patent: Mar. 31, 1992

[54] PROCESS FOR THE PREPARATION OF THIOPHENE DERIVATIVES

[75] Inventors: Steffen Dapperheld, Hofheim am Taunus; Michael Feldhues, Bad Soden am Taunus; Heinz Litterer, Bad Schwalbach; Frank P. Sistig, Hofheim am Taunus; Peter Wegener, Königstein, all of Fed. Rep. of Germany

[73] Assignee: Hoechst Aktiengesellschaft, Frankfurt am Main, Fed. Rep. of Germany

[21] Appl. No.: 474,145

[22] Filed: Feb. 2, 1990

[30] Foreign Application Priority Data

Feb. 6, 1989 [DE] Fed. Rep. of Germany ....... 3903420

[51] Int. Cl.$^5$ ............................................. C25C 1/00
[52] U.S. Cl. ................................. 204/59 R; 204/73 R
[58] Field of Search ................ 204/182.4, 73 R, 59 R; 549/81, 82, 83, 86

[56] References Cited

U.S. PATENT DOCUMENTS 4,588,484 5/1986 Justice, Jr. et al. ............... 204/59 R
4,880,508 11/1989 Aldissi ................................. 204/59 R

FOREIGN PATENT DOCUMENTS 1191088 5/1970 United Kingdom .

OTHER PUBLICATIONS

Gronowitz, S. et al., *Organic Synthesis*, Collective vol. 5, John Wiley & Sons, N.Y., 1973, pp. 149–151.
Gul'tyai, V. P., *Chem. Abs.* 91: 157538h (1979).
Pletcher, D. et al., *J. Appl. Electrochem.* 10:575–582 (1980).
Sosonkin, I. M. et al., *Chem. of Heterocyclic Comps.* 2:1-95–198 (1981) in Engl.: 137–140.
Dettmeier, U. M. et al., *Angew. Chem. Int. Ed.* 26–469 (1987).

*Primary Examiner*—John Niebling
*Assistant Examiner*—Arun S. Phasge

[57] ABSTRACT

Selectively dehalogenated thiophene derivatives are obtained from compounds of the formula II

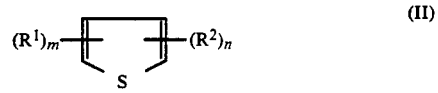

by an electrochemical reaction in a divided electrolysis cell in the presence of a suitable solvent, an onium compound or a compound which is converted into an onium compound in the electrolyte, and a conducting salt. Thiophene derivatives are important intermediates in the production of pharmaceuticals and plant protection agents.

9 Claims, No Drawings

PROCESS FOR THE PREPARATION OF THIOPHENE DERIVATIVES

The invention relates to an electrochemical process for the replacement of halogen atoms in thiophene derivatives by hydrogen or deuterium atoms.

Halogenated thiophene derivatives find wide application as intermediates for the production of pharmaceuticals and plant protection agents.

While the halogenation of thiophene and thiophene derivatives in the 2- and 5-position is carried out simply and even completely halogenated thiophene derivatives can be obtained easily, the preparation of halogenated thiophene derivatives having a free 2- and/or 5-position is difficult.

In general, the synthesis of these thiophene derivatives is carried out by isomerization of halogenated thiophene derivatives on catalysts or by elimination of the halogen atoms in the 2- and 5-position of the thiophene ring of highly halogenated starting materials using reducing agents or organometallic compounds. 3-Substituted thiophenes are obtained as equilibrium mixtures with the starting compounds by isomerization of halogenated thiophene derivatives on acidic catalysts. The isomerization is carried out at comparatively high temperatures and the isomer mixture obtained is then separated (cf. Angew. Chem. Int. Ed. 26 (1987), 468). Suitable reducing agents are, for example, base metals such as zinc which is used in glacial acetic acid to dehalogenate 2,3,5-tribromothiophene to 3-bromothiophene (cf. Organic Synthesis 5 (1973), 149).

The use of metals for dehalogenation is associated with a forced accumulation of metal salts which have to be disposed of. Additionally, the selectivity of the dehalogenation of thiophene derivatives with differing (halogen) substituents is unsatisfactory, as a result of which the utility of the process is limited.

The catalytic dehalogenation of chlorinated thiophene derivatives is also rendered difficult by the formation of salts, since equimolar amounts of bases have to be added. In GB-PS 1,191,088, the dehalogenation of chlorinated thiophenes on noble metal catalysts of group VIII b of the Periodic Table is described, which, in addition to the use of a base, also still requires high temperatures and high pressures.

A process without the forced accumulation of salts, which is carried out at atmospheric pressure and low temperatures, is the electrochemical debromination of 2,3,5-tribromothiophene to 3-bromothiophene. 3-Bromothiophene is obtained in divided electrolysis cells on cathodes of graphite, lead, mercury or zinc, in catholytes of NaBr in dioxane/water and at current densities of at most 50 mA/cm² at the start of the electrolysis. This process is unsuitable for the selective dehalogenation of tetrabromothiophene to 3,4-dibromothiophene, since only the undesired 3-bromothiophene is formed. The selective debromination of 3-methyl-2,3,4-tribromothiophene to either 3-methyl-2,4-dibromothiophene or 3-methyl-4-bromothiophene also does not succeed. 3-Methylthiophene is formed as a product of the complete debromination (cf. J. Appl. Elektrochem. 10 (1980), 575).

The use of a glass diaphragm for the separation of the anode and cathode space in this process has further disadvantages, since the flow cells frequently employed in industry cannot be used. In electrolyte systems which are stirred at a rate customary in industry of about 0.4 m/s, diaphragms cause an incomplete separation of anolytes and catholytes with the result that mixing of the electrolytes may occur. The consequence of this would be that, in the case of the oxidation of bromide ions in the anode space, dissolved bromine would pass through the diaphragm into the cathode space to be reduced there on the cathode to bromide. This may lead to a reduction of the current yield of the cathode reaction and therefore lower the economy of the process distinctly.

The economy of the described process is additionally further reduced by the industrially unusable, technically complicated and expensive control of the electrode potential.

The electrochemical reduction of 2-iodo-5-nitrothiophene and 2-bromo-5-nitrothiophene in dry dimethylformamide on Pt cathodes and with potential control is furthermore described (cf. Chemistry of Heterocyclic Compounds (1981), 137). 2-Nitrothiophene and up to 20% of 2,2'-dinitro-5,5'-dithienyl are found as products.

This process is thus unselective and uneconomical owing to the use of the expensive solvent DMF, the expensive electrode material platinum and the technically complicated potential control.

The electrochemical reduction of 4,5-dimethylthiophene-2-carboxylic acid to 2,5-dihydro-4,5-dimethylthiophene-2-carboxylic acid is furthermore known (cf. Chem. Abstr. 91 (1979), 157538h). A partial hydrogenation of the thiophene basic structure takes place, which in the case of the dehalogenation of halogenated thiophene derivatives would lead to a not inconsiderable lowering of the yield.

From the prior art, the object was therefore to find an economical process for the selective dehalogenation of halogenated thiophene derivatives which could be carried out industrially.

The invention thus relates to a process for the preparation of thiophene derivatives of the formula I

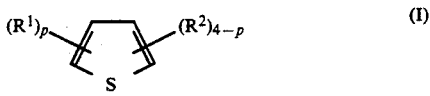

in which

R¹ is identical or different and is a $C_1$–$C_{12}$-alkyl, cycloalkyl, $C_6$-aryl, sulfur-, nitrogen- or oxygen- containing $C_4$-heteroaryl group, a nitrogen- or oxygen-containing $C_5$-heteroaryl, $C_1$–$C_{12}$-alkoxy, cycloalkoxy, $C_6$-aryloxy, sulfur, nitrogen- or oxygen-containing $C_4$-heteroaryloxy group, a nitrogen- or oxygen-containing $C_5$-heteroaryloxy group, $C_1$–$C_{12}$-alkylamino, halogenated $C_1$–$C_{12}$-alkyl, CN or $CH_2OH$ group, a halogen atom or a CO-R³ group, R³ is a hydrogen atom, an OH, OD, $C_1$–$C_6$-alkyl, $C_1$–$C_{12}$-alkoxy or OR⁴ group, R⁴ is an alkali metal, alkaline earth metal or ammonium ion or a $(R^5)_4N^+$ group, R⁵ is a hydrogen atom or a $C_1$–$C_6$-alkyl group, R² is a hydrogen or deuterium atom, p is zero or an integer from 1 to 3, from a compound of the formula II

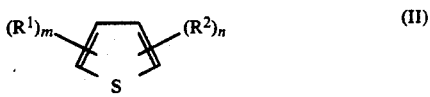

in which
R¹ and R² have the abovementioned meaning and
m is an integer from 1 to 4 and
n is zero or an integer from 1 to 3,
by electrochemical reaction, which comprises carrying out the electrochemical reaction continuously or batchwise in a divided electrolysis cell in an electrolysis liquid consisting of water or one or more organic solvents and of 1 to 70% of a compound of the formula II, relative to the total amount of the catholyte, in the presence of at least one onium compound or a compound which is converted into an onium compound in the electrolyte, which contains at least one nitrogen or phosphorus atom, and in the presence of at least one soluble salt of a metal, having a hydrogen overvoltage of greater than 0.25 V, relative to a current density of 100 mA/cm², on a cathode having a medium to high hydrogen overvoltage at a current density of 10 to 500 mA/cm² and at a temperature of 0° C. up to the boiling point of the electrolyte.

In this electrochemical reaction, R¹ is preferably a $C_1$-$C_6$-alkyl group or a halogen atom, in particular a $C_1$-$C_3$-alkyl group or a halogen atom. R² is preferably an OH, OD, $C_1$-$C_3$-alkyl or $C_1$-$C_6$-alkoxy group, or an $Na^+$, $K^+$, $NH_4^+$ or $(CH_3)_4N^+$ ion.

Starting compounds of the formula II are polyhalogenated thiophene derivatives, preferably completely or partially brominated and/or chlorinated compounds which are derived, for example, from the following substances:

Thiophene, 2- or 3-methylthiophene, 2- or 3-acetylthiophene, 2,4-dimethylthiophene, 2- or 3-thiophenaldehyde, 2- or 3-thiophenecarboxylic acids in the completely or partially chlorinated or brominated form or their methyl, ethyl or propyl esters, sodium, potassium or ammonium salts.

The compounds of the formula II are employed in a concentration of 1% to 70% by weight, preferably 5 to 60% by weight, in particular 5 to 50% by weight, relative to the total amount of the catholyte of an electrochemical cell.

The process according to the invention can be carried out in a divided electrolysis cell at a temperature of 0° C. up to the boiling point of the electrolyte, preferably from 10° to 90° C., in particular from 20° to 80° C., at a current density of 1 to 500 mA/cm², preferably 20 to 400 mA/cm², on a cathode of lead, cadmium, zinc, copper, tin, mercury or an alloy of these metals or carbon in an electrolyte liquid whose liquid medium is composed of water or one or more organic solvents and may contain water. In order to divide the cells into the anode and cathode space, the customary electrolyte-stable diaphragms made of organic polymers such as polyethylene, polypropylene, polyesters and polysulfones, in particular halogen-containing polymers, such as polyvinyl chloride or polyvinylidene fluoride, but preferably perfluorinated polymers, or inorganic materials, such as glass or ceramics, but preferably ion exchange membranes, can be used. Preferred ion exchange membranes are cation exchange membranes made of polymers such as polystyrene, but preferably perfluorinated polymers which contain carboxylic and/or sulfonic acid groups. The use of stable anion exchange membranes is also possible.

The electrolysis can be carried out both continuously and batchwise and in all customary electrolysis cells, such as, for example, in beaker or plate and frame cells or cells with fixed bed or fluid bed electrodes. Both the monopolar and bipolar circuit of electrodes can be used. A procedure in divided electrolysis cells (i.e. with a catholyte and an anolyte liquid) with batchwise implementation of the cathode reaction and continuous operation of the anode reaction is particularly expedient.

According to the invention, cathodes are used which are stable in the electrolyte. The electrode materials used have a medium to high hydrogen overvoltage. The use of carbon cathodes is preferred, in particular for electrolysis in acidic electrolytes having a pH below 4, since some of the electrode materials mentioned, for example Zn, Sn, Cd and Pb, may suffer corrosion.

All known carbon electrode materials can be used as carbon cathodes, for example electrode graphites, impregnated graphite materials, porous graphites, carbon felts, vitreous carbon and also carbon-synthetic composite materials. Polytetrafluoroethylene or polyvinylidene fluoride, for example, are employed as plastics in the composite materials.

All materials customary for anode reactions can be used as anode material. Examples are lead, lead dioxide on lead or other supports, platinum or noble metal oxides, for example ruthenium oxide, doped titanium dioxide on titanium or other materials for the evolution of oxygen from dilute acids such as sulfuric acid, phosphoric acid or tetrafluoroboric acid or carbon or titanium dioxide on titanium doped with noble metal oxides or other materials for the evolution of halogen from aqueous or alcoholic alkali metal halide or hydrogen halide solutions.

Preferred anolyte liquids are aqueous or alcoholic mineral acids or aqueous solutions of their salts, such as dilute sulfuric acid, phosphoric acid, tetrafluoroboric acid, concentrated hydrochloric acid, hydrogen bromide or sodium chloride, ammonium bromide, potassium bromide or sodium bromide solutions, but in particular hydrogen bromide, ammonium bromide, sodium bromide or potassium bromide solutions in water and methanol.

Suitable organic solvents are, for example, short-chain aliphatic alcohols such as methanol, ethanol, n- and iso-propanol or the various butanols, amides such as N,N-dimethylformamide, N-methyl-2-pyrrolidinones, nitriles such as acetonitrile or propionitrile, ketones such as acetone and chlorinated hydrocarbons, such as dichloromethane and chloroform. However, chlorinated aromatic hydrocarbons such as chlorobenzene or chlorotoluene, and also liquid halogenated thiophene derivatives, which can be formed during the electrolysis or added to the catholyte, are also suitable. The prerequisite for utility is that they are not dehalogenated under the reaction conditions, can be separated off easily and are stable. Methanol, ethanol, the various propanols and dichloromethane and halogenated thiophene derivatives, for example 3-bromothiophene, 3,4-dibromothiophene, 3-bromo-4-chlorothiophene, 4-chlorothiophene, 3,4-dichlorothiophene, 3-bromo-4-methylthiophene, 3-bromo-2-methylthiophene and 3-bromo-2,4-dimethylthiophene are preferred. Mixtures can also be used.

A two-phase electrolysis with addition of a water-insoluble organic solvent such as t-butyl methyl ether or methylene chloride in combination with an aqueous electrolyte and an emulsifier is also possible.

Salts of metals having a hydrogen overvoltage of at least 0.25 V (relative to a current density of 100 mA/cm²) and/or dehalogenating properties can furthermore be added to the catholyte. Suitable salts are mainly the soluble salts of Cu, Ag, Au, Zn, Cd, Hg, Sn, Pb, Tl, Ti, Zr, Bi, V, Ta, Cr, Ce, Co or Ni, preferably the soluble Pb, Zn, Sn, Cd and Tl salts. The preferred anions of these salts are $Cl^-$, $Br^-$, $SO_4^{2-}$, $NO_3^-$ and $CH_3COO^-$.

In the choice of anions, care has to be taken that no compounds insoluble in the electrolyte are formed using the cations of the abovementioned metals.

The salts are added to the electrolysis solution or even generated in the solution, for example by adding oxides, carbonates, etc.—in some cases even the metal itself (if soluble). Their concentration in the electrolyte of the undivided cell and in the catholyte of the divided cell is expediently adjusted to about $10^{-3}$ to 10% by weight, preferably to about $10^{-2}$ to 5% by weight, in each case relative to the total amount of the electrolyte or catholyte.

Additionally, one or more compounds, having at least one nitrogen or phosphorus atom, according to the formulae III to VII

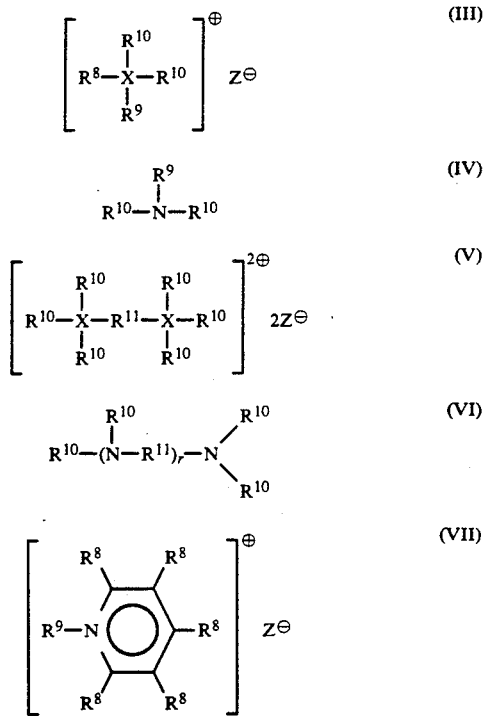

are added to the electrolyte or to the catholyte in which
X is phosphorus or nitrogen,
$R^8$ is hydrogen, alkyl, cycloalkyl, aralkyl having 1 to 18 carbon atoms in the alkyl moiety and aryl having 6 to 12 carbon atoms,
$R^9$ is identical to $R^8$ or is an $(R^8-O)_qR^8$ group and q is an integer from 1 to 12,
$R^{10}$ is identical to $R^8$ or $R^9$ or is a $-(CH_2Y)_r-CH_2-$ group, where r is zero or an integer from 1 to 6, and Y is $-NH$, oxygen, sulfur or $-CH_2-$,
$R^{11}$ is $-(CH_2)_r-$, $-CH_2-[O-(CH_2)_r]_r-O-(CH_2)_2-$ and
Z is an OH group or an anion of an inorganic or organic acid. These acids are, for example, the various hydrohalic acids, sulfuric acid, nitric acid, nitrous acid, phosphoric acid, $H_3BO_3$, $HBF_4$, $HPF_6$, formic acids, acetic acid and oxalic acid.

The compounds I to VII are onium compounds or compounds which are converted into an onium compound in the electrolyte.

The compounds of the formula II to VII are added in concentrations of $10^{-3}$ to 10% by weight, preferably $10^{-2}$ to 5% by weight, relative to the electrolyte or catholyte.

Suitable salts are in particular those with the cations tetramethyl-, tetraethyl-, tetrapropyl- and tetrabutylammonium or -phosphonium, benzyl-, octyl-, decyl-, dodecyl-, tetradecyl-, hexadecyl- or octadeclytrimethylammonium or -trimethylphosphonium, dioctyl-, didecyl-, didodecyl-, ditetradecyl-, dihexadecyl- or dioctadecyldimethylammonium or -dimethylphosphonium, methyltrioctylammonium, N-hexadecylpyridinium and combinations. However, primary, secondary and tertiary amines, from which the onium compounds are formed in the course of the electrolysis, can also be employed. The type of the anions in the onium compounds is unimportant for the process, the halide, sulfate, tetrafluoroborate and hydroxide ions being preferred.

In order to increase the conductivity, inorganic or organic acids can be added to the catholyte, preferably acids such as hydrochloric or hydrobromic acid and sulfuric acid and also acetic acid. When using acids which can form poorly soluble compounds with the abovementioned metals in the neutral or basic range, naturally only those pH ranges are used in which no insoluble compounds are formed.

The addition of bases may also be necessary for setting the pH favorable to the electrolysis and favorably influencing the course of the electrolysis. Suitable bases are primary, secondary and tertiary $C_2-C_{12}$-alkyl-and cycloalkylamines, aromatic and aliphatic-aromatic (in particular araliphatic) amines and their salts, inorganic bases such as alkali metal and alkaline earth metal hydroxides, for example Li, Na, K, Cs, Mg, Ca or Ba hydroxide and mixtures.

The working up of the catholyte can be carried out by distillation in a customary manner. It is particularly advantageous to add water to the electrolytes or catholytes in order to reduce the solubility of the products. In this way, they can be isolated simply after the phase separation. The remaining aqueous solution is extracted to separate off the product residues and is separated into its constituents by distillation. The organic solvents, aqueous acids, the added metal salts and the compounds of the formulae II-VI can be led back into the electrolysis. With hydrogen bromide- or hydrogen chloride-containing solutions, the distillation can be dispensed with, as they are to be used directly as part of the anolyte.

The process according to the invention is illustrated by the following examples.

The electrolysis carried out according to the prior art in a recirculatory cell divided by a cation exchange membrane and dispensing with the control of the electrode potential did not give the desired product in Comparison Example A and in Comparison Example B the reaction did not run selectively and yielded a high proportion of completely dehalogenated product.

In both examples, the solubility of the starting compounds in the catholyte, which was composed of a 0.2 molar solution of sodium bromide in dioxane/water (70:30), was so poor that saturated solutions had to be used, which in one case led to the blocking up of the electrolysis cell.

In both cases, the pH of the catholyte rose to values of greater than 12 in the course of the electrolysis; there was thus the risk that undesired reactions could take place on the thiophene structure or on a substituent.

Finally, the graphite cathode, which is stable to corrosion per se, suffered corrosion damage under the conditions of the comparison examples with the result that use of this method in industry does not appear efficient.

Two types of electrolysis cells were used for the following Examples.

ELECTROLYSIS CELL 1

Plate and frame cell with a 0.02 $m^2$ electrode area. Electrode graphite or impregnated graphite (®Diabon N from Sigri, Meitingen, Germany) was used as the cathode and impregnated graphite or a platinum plate as the anode.

Anolyte: aqueous 15 to 35% strength hydrochloric acid, saturated methanolic hydrochloric acid, methanolic hydrogen bromide solution or 0.5 to 2N aqueous sulfuric acid. The electrode distance was 4 mm and polyethylene gauze was used to maintain the distance. The cation exchange membrane was a two-layer or one-layer membrane made from a copolymer of a perfluorosulfonylethoxyvinyl ether and tetrafluoroethylene (type ®Nafion 324 or 423 from Du Pont, Wilmington, Del., U.S.A.). The flow rate of the electrolyte was 400 l/h.

ELECTROLYSIS CELL 2

Jacketed glass jar cell with a volume of 350 ml and a plastic insert for the anode space.

Cathode: impregnated graphite (®Diabon N from Sigri, Meitingen, Germany);
Anode: platinum gauze, graphite or lead plate (20 $cm^2$);
Cathode area: 12 $cm^2$, electrode distance: 1.5 cm;
Anolyte: as in electrolysis cell 1;
Cation exchange membrane: ®Nafion 324
Substance transport: by magnetic stirrer.

EXAMPLE 1

A catholyte of 2 l of methanol, 500 ml of methylene chloride, 1 g of zinc chloride, 5 g of tetraethylammonium bromide and 159 g of a mixture of 3-methyl-2,4,5-tribromothiophene (95%) and 3-bromomethyl-2,5-dibromothiophene (5%) was electrolysed in the electrolysis cell 1 at a current density of 100 mA/$cm^2$, a voltage of 7 to 8 V and a temperature of 28° to 38° C. The current consumption was 53 Ah. During the electrolysis, the pH of the catholyte was kept at a value between 5 and 7 by addition of a total of 150 g of sodium hydroxide in portions. After addition of 2 l of water to the catholyte, phase separation, extraction with $CF_2Cl-CFCl_2$ and removal of the solvent by distillation, 73.67 g of 3-bromo-4-methylthiophene (yield: 89.9%), 1.47 g of 2,4-dibromo-3-methylthiophene and 2,3-dibromo-4-methylthiophene (yield: 1.2%) and 4.16 g of 3-methylthiophene (yield: 8.9%) were obtained.

EXAMPLE 2

A catholyte of 400 ml of methanol, 200 ml of methylene chloride, 1 g of tin(II) chloride, 5 g of tetramethylammonium chloride and 20.4 g of 2-methyl-3,4,5-tribromothiophene were electrolysed in the electrolysis cell 1 at a current density of 25 mA/$cm^2$, a voltage of 3.8 to 2.9 V and a temperature of 30° C. The current consumption was 8.4 Ah. After addition of 500 ml of water to the catholyte, phase separation and removal of the methylene chloride by distillation, 12.98 g of 3,4-dibromo-2-methylthiophene (yield: 83.1%), 0.45 g of a mixture of 2,3-dibromo-5-methylthiophene and 2,4-dibromo-5-methylthiophene (yield: 2.7%) and 0.071 g of unreacted 2-methyl-3,4,5-tribromothiophene were obtained.

EXAMPLE 3

A catholyte of 1.6 l of methanol, 2 l of methylene chloride, 100 ml of hydrogen bromide solution (48% in water), 6 g of tetramethylammonium chloride, 0.6 g of lead acetate dihydrate and 400 g of 2-methyl-3,4,5-tribromothiophene were electrolysed in the electrolysis cell 1. The current density was 200 mA/$cm^2$ at the start and 100 mA/$cm^2$ at the end of the batch. A voltage of 8 to 7 V was established at temperatures from 35° to 40° C. A further 498 g of 2-methyl-3,4,5-tribromothiophene were added in the course of the electrolysis. 2 l of the catholyte were taken out at regular intervals, water was added and the organic phase was fed back to the catholyte. In order to equalize the loss of conducting salt and lead salt occurring in this way, 6 g of tetramethylammonium chloride and 1 g of lead acetate dihydrate were added to the catholyte. A total of 450 ml of a 25 percent solution of ammonia in water were added to the catholyte in portions to set a pH of 5 to 7. The anolyte was composed of a solution of 2.5 l of methanol, 500 ml of water and 500 ml of HBr solution. It was continuously made up with a total of 4 l of MeOH, 1 l of water and 250 ml of HBr solution and evolved bromine. The batch was worked up as in Example 1 after a current consumption of 888 Ah and 5.05 g of unreacted 2-methyl-3,4,5-tribromothiophene, 469 g of 3,4-dibromo-2-methylthiophene (yield: 68.6%), 21.3 g of a mixture of isomeric dibromomethylthiophenes (yield: 3.1%) and 27.6 g of isomeric bromo-2-methylthiophenes (yield: 5.8%) were obtained.

EXAMPLE 4

A catholyte of 200 ml of methanol, 50 ml of methylene chloride, 5 g of potassium chloride and 8.9 g of 2-methyl-3,4,5-tribromothiophene were electrolysed in the electrolysis cell 2 on a zinc cathode at a current density of initially 83 mA/$cm^2$ and a voltage of 20 to 17 V, and after a current consumption of 2.5 Ah at a current density of 42 mA/$cm^2$ and a voltage of 13.5 V and at a temperature of 30° C. or 24° C. The current consumption was altogether 6.75 Ah.

The batch was worked up as in Example 1. 0.58 g of unreacted 2-methyl-3,4,5-tribromothiophene, 4 g of 3,4-dibromo-2-methylthiophene (yield: 62.9%), 0.37 g of a mixture of isomeric dibromo-2-methylthiophenes (yield: 5.6%) and 0.13 g of a mixture of isomeric bromo-2-methylthiophenes (yield: 0.3%) were obtained. The cathode showed distinct traces of corrosion.

EXAMPLE 5

A catholyte of 2 l of methanol, 1 l of methylene chloride, 50 ml of 48% strength hydrogen bromide solution in water, 20 g of tetraethylammonium bromide and 341 g of 3-methyl-2,4,5-tribromothiophene (of about 91% purity) was electrolysed in the electrolysis cell 1 at a current density of 160 to 180 mA/$cm^2$, a voltage of 8 V and a temperature of 30° to 45° C.

The current consumption was 144 Ah. After addition of 1 l of water to the catholyte and working up as described in Example 1,
204 g of 2,4-dibromo-3-methylthiophene (yield: 80%), 4.9 g of unreacted 3-methyl-2,4,5-tribromothiophene, 4.8 g of 2,3-dibromo-4-methylthiophene (yield: 1.9%), 15.4 g of 4-bromo-3-methylthiophene (yield: 8.7%) and 1.82 g of 2-bromo-3-methylthiophene (yield: 1%) were obtained.

EXAMPLE 6

A catholyte of 3 l of methanol, 1 l of methylene chloride, 2 g of hexadecylpyridinium chloride and 455 g of 3-methyl-2,4,5-tribromothiophene, which contained 18 g of 2,5-dibromo-3-methylthiophene and 22 g of water as impurity was electrolysed in the electrolysis cell 1 at a current density of 50 mA/cm$^2$ at the start of the electrolysis, 8 V terminal voltage and a temperature of 30° C. Within 30 minutes, it was possible to increase the current density to 150 mA/cm$^2$, at a voltage of initially 8 V. In the course of the electrolysis, the voltage fell to 6.1 V.

The current consumption was 236.4 Ah. After addition of 3 l of water to the catholyte and working up as described in Example 1
187.4 g of 3-bromo-4-methylthiophene (yield: 85.4%),
26.4 g of 2,4-dibromo-3-methylthiophene (yield: 8.4%) and
10.7 g of 2-bromo-3-methylthiophene (yield: 4.8%) were obtained.

EXAMPLE 7

A catholyte of 400 ml of methanol, 50 ml of methylene chloride, 0.4 g of lead acetate dihydrate, 12 g of tetramethylammonium chloride and 53 g of 3-methyl-2,4,5-tribromothiophene were electrolysed in electrolysis cell 1 at a current density of 150 mA/cm$^2$ at the start and 50 mA/cm$^2$ at the end of the batch, a voltage of 9 to 7 or 4 V and a temperature from 32° to 35° C. The current consumption was 22 Ah. After addition of 800 ml of water to the catholyte, phase separation, extraction of the aqueous phase with pentane, purification of the organic phases and removal of the solvent by distillation, 3.57 g of unreacted 3-methyl-2,4,5-tribromothiophene, 19.6 g of 3-bromo-4-methylthiophene (yield: 75.5%) and 0.88 g of 3-methylthiophene (yield: 6.1%) were obtained.

EXAMPLE 8

A catholyte of 300 ml of methanol, 100 ml of methylene chloride, 15 g of zinc chloride, 0.5 g of methyltrioctylammonium chloride and 31 g of 3-methyl-2,4,5-tribromothiophene were electrolysed in electrolysis cell 1 at a current density of 50 mA/cm$^2$ at the start and 25 mA/cm$^2$ at the end of the batch, a voltage of 4 or 3 V, a temperature of 34° to 24° C. and pH of −0.8. The current consumption was 14.8 Ah. After addition of 500 ml of water to the catholyte and working up as described in Example 1, 17.4 g of 2,4-dibromo-3-methylthiophene (yield: 73.4%), 0.71 g of 2,3-dibromo-4-methylthiophene (yield: 3%) and 2.92 g of 4-bromo-3-methylthiophene (yield: 17.8%) were obtained.

| Example | 9 | 10 | 11 |
| --- | --- | --- | --- |
| Electrolysis cell | 1 | 1 | 1 |
| Cathode | Impregnated Graphite | Impregnated Graphite | Impregnated Graphite |
| Starting catholyte | 4 l CH$_3$OH<br>0.5 l CH$_2$Cl$_2$<br>10 g (CH$_3$)$_4$NCl<br>1 g Pb(OCOCH$_3$)$_2$.2H$_2$O<br>100 ml HBr(48% in H$_2$O) | 2.5 l C$_2$H$_5$OH<br>0.5 l CH$_2$Cl$_2$ | 1.4 l CH$_2$Cl$_2$<br>0.6 l H$_2$O<br>60 ml HBr.H$_2$O<br>1 g (Pb(OCOCH$_3$)$_2$.2H$_2$O<br>1 g CH$_3$N(C$_8$H$_{15}$)$_3$Cl |
| Tetrabromothiophene [g] | 570 | 80 | 50 |
| Anode | Graphite | Graphite | Graphite |
| Anolyte | CH$_3$OH.HCl | CH$_3$OH.HCl | HBr.H$_2$O |
| Current density [mA/cm$^2$] | 250–100 | 100 | 50–200[1)] |
| Voltage [V] | 8–4.2 | 7–5.5 | 10–22 |
| Temperature [°C.] | 33–50 | 38–42 | 29–34 |
| Current consumption [Ah] | 142.4 | 46.4 | 76 |
| Electrolysis result | | | |
| 2,3,4-Tribromothiophene [g] (Yield) | 23.4 (4.9%) | 1.4 (2.2%) | — |
| 3,4-Dibromothiophene | 301 (87.0%) | 29.5 (61%) | 10.4 (34.3%) |
| 3-Bromothiophene | 9.2 (7.6%) | 1.5 (4.7%) | 8.22 (40.3%) |

| Example | 12 | 13 | 14 |
| --- | --- | --- | --- |
| Electrolysis cell | 1 | 1 | 1 |
| Cathode | Impregnated Graphite | Graphite | Lead[3)] |
| Starting catholyte | 2 l CH$_3$OH<br>0.5 l CH$_2$Cl$_2$<br>100 ml HBr.H$_2$O<br>1 g Pb(OOCH$_3$)$_2$.2H$_2$O<br>2 g C$_{12}$H$_{25}$NH$_2$ | 100 ml CH$_3$OH<br>50 ml CH$_2$Cl$_2$<br>0.5 g CdCl$_2$ | 100 ml CH$_3$OH<br>50 ml CH$_3$CN<br>10 ml HBr.H$_2$O |
| Tetrabromothiophene [g] | 50 | 10 | 10 |
| Anode | Graphite | Pt | Pt |
| Anolyte | HBr.CH$_3$OH/H$_2$O[2)] | HBr.CH$_3$OH | HBr.CH$_3$OH |
| Current density [mA/cm$^2$] | 100–50 | 83 | 83 |
| Voltage [V] | 6–5.5 | 13.5–11.5 | 8–10 |
| Temperature [°C.] | 32 | 35 | 30 |
| Current consumption [Ah] | 51.2 | 5.06 | 13.6[4)] |
| Electrolysis result | | | |
| 2,3,4-Tribromothiophene [g] (Yield) | — | 0.036 (0.4) | 0.39 (9.2) |
| 3,4-Dibromothiophene | 21.85 (71.3%) | 5.39 (89.2%) | 3.21 (53.2%) |

| | | |
|---|---|---|
| 3-Bromothiophene | 2.8 (13.8%) | 0.056 (13.8%) 1.14 (14%) |

[1] after adjustment to pH 9 by addition of NaOH
[2] worked-up catholyte from Example 11
[3] Corrosion of the cathode
[4] 7 by-products
Working up was carried out as in Example 1.

EXAMPLE 15

A catholyte of 2 l of methanol, 50 ml of hydrogen bromide solution (48% in water), 50 ml of ammonia solution (25% in water), 0.6 g of lead acetate dihydrate, 5 g of methyltrioctylammonium chloride and 128 g of a mixture of brominated thiophenes, which are obtained in the purification of tetrabromothiophene and are intended to be converted to 3-bromothiophene or thiophene, composed of 23.24% of tetrabromothiophene, 35.0% of isomeric tribromothiophenes and 39.5% of isomeric dibromothiophenes, were electrolysed in electrolysis cell 1. The anolyte was composed of a solution of ammonia in methanol. At a current density of 50 mA/cm$^2$ and temperatures from 38° to 56° C., an amount of charge of 122.4 Ah was consumed at a voltage of 23 V at the beginning and 7 V at the end of the batch. For working up, 2 l of water were added to the catholyte, the mixture was extracted with CF$_2$Cl—CFCl$_2$ and the extract was freed from adhering ammonia using dilute hydrochloric acid. After removal of the solvent by distillation, 55.75 g of 3-bromothiophene (yield: 81.8%) and 4.62 g of thiophene (yield: 13.1%) were obtained.

EXAMPLE 16

A catholyte of 450 ml of methanol, 150 ml of methylene chloride, 0.6 g of lead acetate dihydrate, 5 g of tetrabutylphosphonium bromide and 20 g of 2-chloro-3,4,5-tribromothiophene were electrolysed in electrolysis cell 1 at a current density of 50 mA/cm$^2$ at the beginning and 25 mA/cm$^2$ at the end of the batch, at a voltage of 5.1 to 3 V and a temperature of 29°–49° C. After the addition of 500 ml of water, phase separation, extraction of the aqueous phase with CF$_2$Cl—CFCl$_2$, purification of the organic phases and removal of the solvent by distillation, 8.74 g of 2-chloro-3,4-dibromothiophene (yield: 56.6%), 0.6 g of a 2-chloro-dibromo-thiophene of unknown structure (yield: 3.75%), 2.7 g of iosmeric dibromothiophenes (yield: 10.8%) and 0.6 g of 2,3,4-tribromothiophene (yield: 3.1%) were obtained.

EXAMPLE 17

A catholyte of 650 ml of methanol, 0.5 g of lead acetate dihydrate, 0.5 g of tetrabutylammonium tetrafluoroborate, 20 ml of hydrogen bromide solution (48% in water) and 20 g of 3-chloro-2,4,5-tribromothiophene were electrolysed in electrolysis cell 1 at a current density of 100 mA/cm$^2$ at the beginning and 25 mA/cm$^2$ at the end of the batch, a voltage of 7.2 to 3.4 V and a temperature of 28° to 35° C. The current consumption was 8.8 Ah. After addition of 100 ml of water to the catholyte, extraction with CF$_2$Cl—CFCl$_2$ and removal of the solvent by distillation, 8.24 g of 4-bromo-3-chlorothiophene (yield: 73.8%), 0.665 g of 3-chlorothiophene (yield: 9.1%) and 0.4 g of dibromothiophene of unknown structure (yield: 2.9%) were obtained.

EXAMPLE 18

A catholyte of 4 l of methanol, 1 l of methylene chloride, 2 g of lead acetate dihydrate, 20 g of tetramethylammonium chloride, 100 ml of hydrogen bromide solution (48% in water) and 300 g of a mixture of 258 g of 3-chloro-2,4,5-tribromothiophene and 42 g of tetrabromothiophene were electrolysed in electrolysis cell 1 at a current density of 200 mA/cm$^2$, a voltage of 14 V and a temperature of 38° C.

After dissolution of the suspended starting material and formation of partially dehalogenated liquid thiophene derivatives, it was possible to add 1600 g of starting material of the abovementioned composition in portions. The current density was lowered to 50 mA/cm$^2$ and a temperature of 30°–32° C. was established at a voltage of 4 to 4.5 V.

After a charge consumption of 1318 Ah, the same amount of water was added to the catholyte and the product was isolated.

872 g of 3-bromo-4-chlorothiophene (yield: 96.3%, relative to 3-chloro-2,4,5-tribromothiophene employed), 8.86 g of 4-chloro-2,3-dibromothiophene (yield: 0.6%, relative to 3-chloro-2,4,5-tribromothiophene employed), 2.69 g of 2,3,4-tribromothiophene, (yield: 1.3%, relative to 3-chloro-2,4,5-tribromothiophene employed) and 126.6 g of 3,4-dibromothiophene (yield: 78.8%, relative to tetrabromothiophene employed), were obtained.

EXAMPLE 19

A catholyte of 200 ml of methanol, 5 g of tetrabutylphosphonium bromide, 0.4 g of TlCl and 10 g of 2-acetyl-5-bromothiophene were electrolysed in electrolysis cell 2 at a current density of 83 mA/cm$^2$, a voltage of 23 to 10 V and a temperature of 30° C. The current consumption was 6.3 Ah.

The anolyte was composed of a solution of sulfuric acid in methanol, and a platinum wire was used as the anode. For working up, 200 ml of water were added to the catholyte and the mixture was extracted with pentane. After removal of the solvent by distillation, 4.28 g of 2-acetylthiophene (yield: 77.7%) and 1.04 g of unreacted 2-acetyl-5-bromothiophene were obtained.

EXAMPLE 20

A catholyte of 2 l of methanol, 20 g of tetramethylammonium chloride, 0.3 g of lead acetate dihydrate, 50 ml of 25% strength ammonia solution in water and 1 kg of a solution composed of 0.883 kg of 3-bromothiophene, 0.101 kg of 2-bromothiophene and 0.016 kg of thiophene were electrolysed in electrolysis cell 1.

The anolyte was composed of a solution of 10% ammonium bromide in methanol.

Up to a charge consumption of 26 Ah, the current density was 200 mA/cm$^2$, up to 115 Ah, it was 100 mA/cm$^2$ and using 50 mA/cm$^2$, the batch was electrolysed up to a charge consumption of 131 Ah.

At temperatures of 52° or 42° to 44° C., the voltage was 16 or 9 to 11 and finally 6 V.

The pH was 7.7.

After addition of 3 l of water to the catholyte and phase separation, and also extraction of the aqueous phase with CF$_2$Cl—CFCl$_2$ and removal of the solvent by distillation,
0.865 kg of 3-bromothiophene,
0.002 kg of 2-bromothiophene and
0.066 kg of thiophene were obtained.

COMPARISON EXAMPLE A

A catholyte of 1.4 l of dioxane, 600 ml of water, 40.8 g of sodium bromide and 50 g of tetrabromothiophene was electrolysed in electrolysis cell 1 at a current density of 150 mA/cm$^2$, a voltage of 23 to 11 V and a temperature of 55° C.

At the start of the electrolysis, only a small part of the starting compound was soluble in the electrolyte with the result that blocking up of the electrolyte channels in the electrolysis cell occurred. After increasing the temperature to 70° C. and adding the starting compound in small portions, these problems no longer occurred. In the anolyte, 2.1 ml of dioxane, 900 ml of water and 62 g of sodium bromide were electrolysed on a graphite anode. In the course of the electrolysis, a further 100 g of sodium bromide were added. The current consumption was altogether 91.2 Ah, and 63% of the amount of charge was consumed in the formation of hydrogen.

The composition of the catholyte was analyzed twice in the course of the electrolysis.

|  | 1 | 2 |
| --- | --- | --- |
| Current consumption | 63.2 Ah | 91.2 Ah |
| Tetrabromothiophene | 25.4% | 6.2% |
| 2,3,4-tribromothiophene | 1.7% | — |
| 3,4-dibromothiophene | 12.9% | 2.8% |
| 3-bromothiophene | 48.7% | 90.9% |

For working up, the procedure was as in Example 1. The isolation of the product was made difficult by poor phase separation and stable emulsions. After extracting the solution seven times with CF$_2$Cl—CFCl$_2$ and separating off the solvent, 20 g of a mixture of 4.6 g of dioxane, 14 g of 3-bromothiophene (yield: 70%), 0.95 g of unreacted tetrabromothiophene and 0.45 g of 3,4-dibromothiophene (yield: 1.5%) were obtained.

COMPARISON EXAMPLE B

A catholyte of 500 ml of dioxane, 200 ml of water, 14.4 g of sodium bromide and 15 g of 3-methyl-2,4,5-tribromothiophene was electrolysed in electrolysis cell 1 at a current density of 50 mA/cm$^2$, a voltage of 10.6 to 9.2 V and a temperature of 28° to 36° C. on a cathode of graphite. 20.6 g of sodium bromide in 700 ml of dioxane and 300 ml of water were oxidized in the anolyte on an anode of platinum.

The current consumption was 11.2 Ah and the pH of the catholyte rose from 2.4 at the start of the electrolysis to 12.5. In the course of the electrolysis, the catholyte became dark-colored, which was traced back to suspended graphite particles which originated from the corrosion of the cathode.

For working up, the procedure was as in Comparison Example 1. 6.8 g of a mixture of various products were obtained:
0.66 g of unreacted 3-methyl-2,4,5-tribromothiophene,
0.43 g of 3-methyl-2,4-dibromothiophene (yield: 9.7%),
4.88 g of 4-bromo-3-methylthiophene (yield: 64.1%),
0.1 g of 2-bromo-3-methylthiophene (yield: 1.2%) and
0.7 g of the undesired, completely dehalogenated 3-methylthiophene (yield: 16.3%).

We claim:
1. A process for the preparation of thiophene derivatives of the formula I

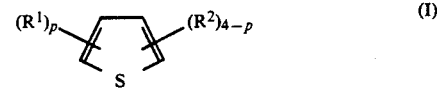

in which
R$^1$ is identical or different and is a C$_1$-C$_{12}$-alkyl, cycloalkyl, C$_6$-aryl, C$_1$-C$_{12}$-alkoxy, cycloalkoxy, C$_6$-aryloxy, C$_1$-C$_{12}$-alkyl-amino, halogenated C$_1$-C$_{12}$-alkyl, CN or CH$_2$OH group, a halogen atom or a CO—R$^3$ group, R$^3$ is a hydrogen atom, an OH, OD, C$_1$-C$_6$-alkyl, C$_1$-C$_{12}$-alkoxy or OR$^4$ group, R$^4$ is an alkali metal, alkaline earth metal or ammonium ion or a (R$^5$)$_4$N$^+$ group, R$^5$ is a hydrogen atom or a C$_1$-C$_6$-alkyl group,
R$^2$ is a hydrogen or deuterium atom,
p is zero or an integer from 1 to 3,
from a completely or partially chlorinated and/or brominated derivative of a compound of the formula II

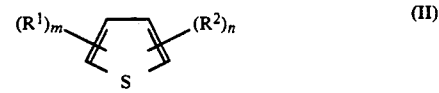

in which
R$^1$ and R$^2$ have the abovementioned meaning and
m is an integer from 1 to 4 and
n is zero or an integer from 1 to 3 and at the same time n=4-m
by electrochemical dehalogenation, which comprises carrying out the electrochemical reaction continuously or batchwise in a divided electrolysis cell in an electrolysis liquid comprising of water or one or more organic solvents and 1 to 70% of a compound of the formula II, relative to the total amount of the catholyte, in the presence of at least one onium compound or a compound which is converted into an onium compound in the electrolyte, which contains at least one nitrogen or phosphorus atom, and in the presence of at least one soluble salt of a metal, having a hydrogen overvoltage of greater than 0.25 V, relative to a current density of 100 mA/cm$^2$, on a cathode having a medium to high hydrogen overvoltage at a current density of 10 to 500 mA/cm$^2$ and at a temperature of 0° C. up to the boiling point of the electrolyte.

2. The process as claimed in claim 1, which comprises using methanol, ethanol, the various propanols, dichloromethane and halogenated aromatic compounds as organic solvents.

3. The process as claimed in claim 1, which comprises using compounds of the formulae III to VII

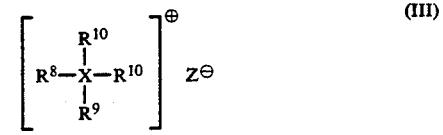

-continued

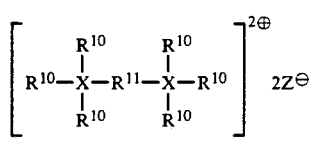
(V)

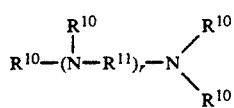
(VI)

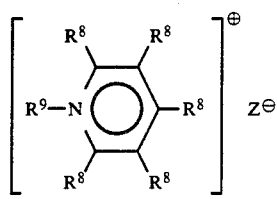
(VII)

in which

X is phosphorus or nitrogen, $R^8$ is hydrogen, alkyl, cycloalkyl, aralkyl having 1 to 18 carbon atoms in the alkyl moiety and aryl having 6 to 12 carbon atoms, $R^9$ is identical to $R^8$ or is an $(R^8-O)_q R^8$ group and q is an integer from 1 to 12, $R^{10}$ is identical to $R^8$ or $R^9$ or is a $-(CH_2Y)_r-CH_2-$ group, r is zero or an integer from 1 to 6, and Y is $-NH$, oxygen, sulfur or a $-CH_2-$ group, $R^{11}$ is $-(CH_2)_r-$, $-CH_2-[O-(CH_2)_r]_r-O-(CH_2)_2-$ and Z is an OH group or an anion of an inorganic or organic acid, in concentrations of $10^{-3}$ to 10%, relative to the total amount of the catholyte.

4. The process as claimed in claim 1, which comprises adding salts of the metals lead, zinc, tin, cadmium or thallium in concentrations of $10^{-3}$ to 10%, relative to the total amount of catholyte, to the catholyte, the anions being $Cl^-$, $Br^-$, $SO_4^{2-}$, $NO_3^-$, $CH_3COO^-$ and $PO_4^{3-}$.

5. The process as claimed in claim 1, which comprises electrolysing on cathodes of lead, zinc, tin, cadmium, copper, mercury or alloys of these metals or carbon.

6. The process as claimed in claim 1, which comprises electrolysing in acidic catholytes on a cathode of carbon.

7. The process as claimed in claim 1, which comprises employing electrode graphites, impregnated graphites, porous graphites, carbon felts, vitreous carbon or carbon-synthetic composite materials as the carbon electrode.

8. The process as claimed in claim 1, which comprises using aqueous or alcoholic solutions of hydrohalic acids as the anolyte.

9. The process as claimed in claim 1, which comprises electrolysing in a cell divided by a cation or anion exchange membrane.

* * * * *